United States Patent [19]

Chen

[11] Patent Number: 6,077,512

[45] Date of Patent: Jun. 20, 2000

[54] EXTERNALLY-APPLIED MEDICINE FOR CURING BLACK FOOT DISEASE

[76] Inventor: Ren-Rong Chen, 47, Chung Hsiao Street, Hwa Lian City, Taiwan

[21] Appl. No.: 08/497,169

[22] Filed: Jun. 30, 1995

Related U.S. Application Data

[63] Continuation of application No. 08/135,401, Oct. 13, 1993, abandoned.

[51] Int. Cl.[7] ..................................................... A61K 35/78
[52] U.S. Cl. ........................................ 424/195.1; 514/887
[58] Field of Search .......................... 424/195.1; 514/887

[56] References Cited

U.S. PATENT DOCUMENTS 5,595,743  1/1997  Wu ........................................ 424/195.1

Primary Examiner—Jyothsna Venkat

Attorney, Agent, or Firm—Bacon & Thomas

[57] ABSTRACT

An externally-applied medicine for curing black foot disease comprising a basis part consisting of equal amount of ground, powdered, and mixed clove, frankincense, myrrha, rhizama arisaematis, pinellia, monkshood (root) or kusnezoff monkshood (root), and tuber of bamboo-leaved orchid, and an adjuvant part consisting of equal amount of round, powdered, and mixed borneol, powdered soy bean, borax, coptis root and/or phellodendron amureuse, and sepia aculeata. The medicine is used in such a manner that the powdered basis part is mixed and stirred with tea water until it becomes plaster-like, and the adjuvant part is scattered in dry form onto the wound or swollen area caused by the black foot disease before the plaster-like basis part is applied to the wound or swollen area about 0.5 cm in thickness. The wound is then bandaged and the medicine is renewed once to twice a day until fresh flesh appears in the wound. Thereafter, the medicine is continuously applied but in a dry form until the wound is completely healed.

9 Claims, No Drawings

EXTERNALLY-APPLIED MEDICINE FOR CURING BLACK FOOT DISEASE

This application is a Continuation of application Ser. No. 08/135,401, filed Oct. 13, 1993 now abandoned.

BACKGROUND OF THE INVENTION

The present invention relates to an externally-applied medicine for curing a special disease found in southern Taiwan area which is usually known as the black foot disease.

The black foot disease is an endemic disease caused by a kind of arsenism, and is normally found in Taiwan coastal areas having highly salty land, such as the Pei-Man Hsian of Tainan Hsien and the Pu-Dai Town and Tong-Shih Hsian of Chia Yi Hsien. All of these areas are located at southwest coastal plain of Taiwan. However, the same disease is also found in other places through the entire Taiwan.

The symptom of this disease at early stage is some kind of carbuncle, putrilaginous pustule or black pimple-like carbuncle. When such carbuncle or pustule is pierced and broken, the wound is black in color and is sometimes filled with pus and has ropy fluid or thin blood effusing from the wound. After the wound becomes putrefied, it looks like having a layer of black satin thereon. Because such carbuncle or putrilaginous pustule is mostly found on the patient's feet, the disease is usually called as the black foot disease. However, cases that such carbuncle or pustule appears at patient's other areas are found, too. Apart from the black and purulent wound, and the continuous effusion of ropy fluid and thin blood, the black satin-like layer formed on the putrefied wound is a special feature of this disease which will appear again in the next day even if it is removed. The worsened wound gradually expands with unacceptable stink, swelling and pain, seriously bothering the patient who might even suffer long term of insomnia. Since no effective medicine has been developed for the black foot disease up to now, the only way to help the patient to temporarily escape from the agonizing pain is to amputate the suffering foot or feet. However, there is still possibility that the disease appears at other areas of the patient.

It is therefore tried by the applicant based on his years experiences in the research of Chinese medicine and clinical tests to develop a magical prescription to effectively cure the horrible black foot disease.

SUMMARY OF THE INVENTION

A primary object of the present invention is to provide a curative medicine which is based on a special recipe including several different kinds of Chinese medicine material ground to powder and can be easily applied to the wounds caused by the black foot disease. The curative medicine for curing black foot disease according to the present invention consists of a basis part and an adjuvant part. The basis part is mixed with tea water and stirred to plaster before it is used to cover the wound. The adjuvant part is scattered in a dry form on the wound and/or swollen area before the plaster of basis part is applied to the wound. The curative medicine according to the present invention can immediately kill pain, stop bleeding, stop itching, remove stink, eliminate cacodes, drain pus and help the growth of new tissue around the wound. The patient may get rid of the troublesome insomnia with the gradually stabilized condition. The gangrenous muscle and skin caused by the black foot disease will be gradually healed and the amputation can be avoided.

DETAILED DESCRIPTION OF THE INVENTION

The externally-applied medicine for curing the black foot disease according to the present invention consists of a basis part and an adjuvant part. The basis part of the medicine is the powder ground and mixed from equal amount of clove, frankincense, myrrha, rhizama arisaematis, pinellia, monkshood (root) or kusnezoff monkshood (root), and tuber of bamboo-leaved orchid. The rhizama arisaematis and pinellia must be soaked in water so as to remove their slickness. The monkshood (root) or kusnezoff monkshood (root) can be added only when the wound becomes seriously swollen and can be used alone or combined together. The adjuvant part of the medicine is the powder ground and mixed from equal amount of borneol, powdered soy bean, borax, coptis root, phellodendron amureuse, and sepia aculeata. The borax must be calcined, and the sepia aculeata must be removed of the hard shell and be soaked in water to remove the salt contained therein.

When using the medicine of the present invention, first wash clean the wound with tea water or alcohol, then scatter the dry and powdered adjuvant part of the medicine onto the wound or swollen area on the patient's skin; secondly, mix and stir the powdered basis part of the medicine with tea water until the basis part becomes plaster, then apply the wet plaster of basis part to the wound which has been scattered with the adjuvant part. The entire wound and the swollen area must be covered by the wet plaster of the basis part to a thickness about 0.5 cm. The plastered wound is then bandaged. The wet plastered basis part and the dry powdered adjuvant part are renewed once a day. For worse wound effusing ropy fluid and thin blood, it is preferable to renew the medicine twice a day. When the black slough in the wound is gradually removed and the fresh muscle appears, both the basis part and the adjuvant part are continuously applied to the wound but in a dry form until the wound is completely healed.

Since the rhizama arisaematis and pinellia included in the basis part and the borax in the adjuvant part are of toxicant, the medicine of the present invention is absolutely limited to external use. The medicine of the present invention can not be orally or internally taken.

Moreover, the medicine of the present invention is also an excellent medicine to cure the breast cancer, neck cancer, epactal cartilage, stasis of blood, bruise, swelling, fracture, and other trauma, swelling and pain caused by falling or serious impact.

The medicine of the present invention for curing the black foot disease has been proven to have excellent effect in many clinical experiments and the voluntary revolving medical services sponsored by the Tainan Regiment Control Area Command and the Taitung Division Control Area Command of the Ministry of National Defense of the Republic of China.

What is claimed is:

1. A topical two-part medicinal composition for treating black foot disease which comprises a powdered adjuvant part for sprinkling onto affected portions of an individual suffering from black foot disease and a basis part for adhesion to affected portions of said individual when mixed with tea water; said adjuvant part being a dry powder mixture formed from equal amounts of borneol, soy bean, calcined borax, coptis root, phellodrendron amureuse and de-shelled desalted sepia aculeata; said basis part being a powder mixture containing equal amounts of clove, frankincense, myrrha, de-slicked rhizama arisaematis, de-slicked pinellia and tuber of bamboo-leaved orchid.

2. The composition of claim 1 which further includes monkshood root and said basis part is a powder containing equal amounts of clove, frankincense, myrrha, de-slicked rhizama arisaematis, de-slicked pinellia, tuber of bamboo-leaved orchid and monkshood root.

3. The composition of claim 1 which further includes kusnezoff monkshood root and said basis part is a powder containing equal amounts of clove, frankincense, myrrha, de-slicked rhizama arisaematis, de-slicked pinellia, tuber of bamboo-leaved orchid and kusnezoff monkshood root.

4. The composition of claim 1, wherein the basis part is in admixture with an effective amount of tea water so that said admixture is in the form of a plaster for adhesion to affected portions of said individual.

5. The composition of claim 4 which further includes monkshood root and the basis part includes equal amounts of clove, frankincense, myrrha, de-slicked rhizama arisaematis, de-slicked pinellia, tuber of bamboo-leaved orchid and monkshood root.

6. The composition of claim 4 which further includes monkshood root and the basis part includes equal amounts of clove, frankincense, myrrha, de-slicked rhizama arisaematis, de-slicked pinellia, tuber of bamboo-leaved orchid and kusnezoff monkshood root.

7. A method for treating black foot disease with a two part topical composition containing a basis part and an adjuvant part; said adjuvant part being a dry powder mixture formed from equal amounts of borneol, soybean, calcined borax, coptis root, philodendron amureuse and de-shelled desalted sepia aculeata and said basis part being a powder mixture containing equal amounts of clove, frankincense, myrrha, de-slicked rhizama arisaematis, de-slicked pinellia and tuber of bamboo-leaved orchid; said method comprising the sequential steps of:

a) cleaning the diseased tissue of an individual suffering from said disease;

b) sprinkling said adjuvant part onto said diseased tissue;

c) spreading an adherent coating of a plaster about 0.5 cm thick onto said diseased tissue; said plaster being formed by mixing said basis part with an effective amount of tea water so as to form a wet mixture having a consistency for application to the body by adhesion thereto;

d) applying a bandage over said plaster coated diseased tissue;

e) periodically replacing said adjuvant part and plaster at least about once a day until the diseased tissue is sloughed off and then;

f) maintaining said diseased tissue in contact with said adjuvant part and basis part in dry form until healing is complete.

8. The method of claim 7, wherein the basis part further includes monkshood root and said basis part is a powder containing equal amounts of clove, frankincense, myrrha, de-slicked rhizama arisaematis, de-slicked pinellia, tuber of bamboo-leaved orchid and monkshood root.

9. The method of claim 7 wherein the basis part further includes kusnezoff monkshood root and said basis part is a powder containing equal amounts of clove, frankincense, myrrha, de-slicked rhizama arisaematis, de-slicked pinellia, tuber of bamboo-leaved orchid and kusnezoff monkshood root.

* * * * *